United States Patent
Diethelm et al.

(10) Patent No.: US 12,364,482 B2
(45) Date of Patent: Jul. 22, 2025

(54) PROTECTIVE COVER FOR A SURGICAL INSTRUMENT

(71) Applicant: IMD TECH GMBH, Tettnang (DE)

(72) Inventors: Nils Diethelm, Schattdorf (CH); Benjamin Diethelm, Zürich (CH)

(73) Assignee: IMD TECH GMBH, Tettnang (DE)

( * ) Notice: Subject to any disclaimer, the term of this patent is extended or adjusted under 35 U.S.C. 154(b) by 0 days.

(21) Appl. No.: 18/840,110

(22) PCT Filed: Feb. 16, 2023

(86) PCT No.: PCT/EP2023/053878
§ 371 (c)(1),
(2) Date: Aug. 21, 2024

(87) PCT Pub. No.: WO2023/161117
PCT Pub. Date: Aug. 31, 2023

(65) Prior Publication Data
US 2025/0032120 A1 Jan. 30, 2025

(30) Foreign Application Priority Data
Feb. 24, 2022 (EP) ..................................... 22158649

(51) Int. Cl.
*A61B 17/064* (2006.01)
*A61B 17/115* (2006.01)

(52) U.S. Cl.
CPC .............................. *A61B 17/1155* (2013.01)

(58) Field of Classification Search
CPC ................................................ A61B 17/1155
See application file for complete search history.

(56) References Cited

U.S. PATENT DOCUMENTS

| 5,404,870 A | 4/1995 | Brinkerhoff et al. |
| 7,182,239 B1 | 2/2007 | Myers |
| (Continued) | | |

FOREIGN PATENT DOCUMENTS

| DE | 202015003135 U1 | 5/2015 |
| DE | 20 2015 003 133 U1 | 6/2015 |
| (Continued) | | |

OTHER PUBLICATIONS

Apr. 14, 2023 International Search Report issued in International Patent Application No. PCT/EP2023/053878.
(Continued)

*Primary Examiner* — Eyamindae C Jallow
(74) *Attorney, Agent, or Firm* — Oliff PLC (57) ABSTRACT

A protective cover for a surgical instrument including an outer sheath for at least partially covering a head region of the surgical instrument inserted into the protective cover along its longitudinal axis, and a pulling device which is connected to the outer sheath in a force-transmitting manner and comprises a pulling element. The outer sheath has a dividing line which divides the outer sheath into at least a first segment and a second segment, wherein the first segment and the second segment are connected to one another by a connecting piece and can be transferred from a covering position into a release position of the head region with the aid of the pulling device. The outer sheath includes an orientation device arranged in its distal apex region and centered on the longitudinal axis, which is designed as a thickening of the apex region.

14 Claims, 4 Drawing Sheets

(56) References Cited

U.S. PATENT DOCUMENTS

| | | | |
|---|---|---|---|
| 8,353,438 B2 | 1/2013 | Baxter, III et al. | |
| 8,622,275 B2 | 1/2014 | Baxter, III et al. | |
| 8,662,370 B2 * | 3/2014 | Takei | A61B 17/115 227/179.1 |
| 11,642,131 B2 * | 5/2023 | Williams | A61B 17/1155 227/179.1 |
| 2005/0143756 A1 | 6/2005 | Jankowski | |
| 2011/0114699 A1 * | 5/2011 | Baxter, III | A61B 17/1155 227/175.1 |
| 2011/0248067 A1 | 10/2011 | Takei | |

FOREIGN PATENT DOCUMENTS

| | | |
|---|---|---|
| EP | 2039316 A2 | 3/2009 |
| EP | 2730237 A1 | 5/2014 |
| EP | 2962648 A1 | 1/2016 |
| WO | 0200121 A1 | 1/2002 |
| WO | 2007/147439 A1 | 12/2007 |
| WO | 2011/063056 A2 | 5/2011 |
| WO | 2016174088 A1 | 11/2016 |

OTHER PUBLICATIONS

Apr. 14, 2023 Written Opinion issued in International Patent Application No. PCT/EP2023/053878.

* cited by examiner

PROTECTIVE COVER FOR A SURGICAL INSTRUMENT

The invention relates to a protective cover for a surgical instrument, in particular for a stapler or a circular stapler, according to the general term of claim 1.

In minimally invasive surgical procedures, various surgical instruments are used that have been specially developed for this application, e.g. staplers, in particular circular staplers. Staplers combine various functionalities at one point of use. Staplers are mainly designed to create a suture between tissue parts of an organ, e.g. a bowel. Depending on the type of device, a stapler can also be used to remove parts of diseased or damaged organs, make incisions in organs and tissues, create connections between hollow organs or clamp blood vessels.

For this purpose, the stapler used here has a counterpart that is sewn into the opposite half of the vessel by stapling before the two halves of the tissue are actually joined. The counterpart is also known in the professional world as anvil cap. Furthermore, the stapler has an axially displaceable mandrel which pierces the end face of one of the two tissue halves previously closed by means of a longitudinal seam and is then inserted into a hollow shaft of the counterpart. By pulling back the mandrel, the two tissue halves are braced against each other so that when the stapler is triggered, the staples create an annular seam that connects the two tissue halves.

Furthermore, the stapler has a ring-shaped knife that can act as a punching tool and opens the previously closed tissue halves after the seam has been made, thus restoring the free lumen of the tissue.

The stapler has a front part, in particular a head region, which often has a sharp-edged shape, as can be the case with the front part of other surgical instruments. As a result, it can sometimes be difficult to insert the surgical instrument into the patient's body and position it precisely at the site of use. In addition, when the stapler is advanced, for example, there is a risk that the surrounding tissue will be damaged by the operation, which could extend the patient's recovery time and, in particular, lead to secondary diseases.

WO 2007/147439 A1 discloses a device for inserting and positioning a surgical instrument into the body of a patient at an operation site, comprising an outer sheath. At least a front part of the surgical instrument is insertable into the outer sheath, which is removable at the operation site. An opening of the outer sheath can be created by means of a pulling arrangement and perforations at the tip of the outer sheath. The outer sheath can be pulled back in one piece over the front part of the surgical instrument by means of the pulling arrangement after the perforations have been torn.

DE 20 2015 003 133 U1 discloses a protective cover for a surgical instrument, in particular for staplers, comprising an outer sheath which is arranged in such a way that it can at least partially cover a head region of the surgical instrument. Furthermore, the protective cover comprises an actuating device which is connected to the outer sheath in a force-transmitting manner and is formed from at least one pulling element. The outer sheath is formed from a first segment and a second segment, whereby the first segment and the second segment can be moved from a covering position to a release position with the aid of the actuating device. The first segment and the second segment remain connected to each other by at least one joint during the transfer from the covering position to the release position.

WO02/00121 discloses an anti-slip protection for a housing head of medical instruments, which consists of a closing device comprising two sections. The sections are connected to one another at their outer connecting line by means of web-shaped plug-in bridges and touch one another when the closing device is inserted. On the outside of the two sections, two fastening devices of pulling device are provided in the lower area, which are designed as recessed fastening eyelets. A tear-proof cord is tied to each of these fastening eyelets. During a separation and removal process of the anti-slip protection from the housing head, the operator can move a connecting pin out of the interior of the housing head by means of a rotating device mounted in a housing handle of the medical instrument. A tip of the connecting pin enters a guide recess formed in the contact surface of the closing device and pushes the two sections apart as it is unscrewed further until the backs of the two sections are separated. In this way, the anti-slip protection separates into two sections of the same design, which are removed from the intestinal section one after the other by pulling the cords.

The above-mentioned devices provide a protective cover for a surgical instrument, in particular for a stapler, which does not, however, provide any help in positioning the head region of the surgical instrument. In the case of the stapler, the counterpart and the mandrel must be centered relative to each other before an annular suture can be created by stapling. The protective covers mentioned above do not allow to determine the location where the mandrel will pierce the tissue halves for insertion into the counterpart. It follows that several attempts may be necessary to find the optimal relative position of the counterpart and the mandrel. Another complicating factor is that the head region can get caught in tissue folds during the movements of the surgical instrument during the attempts.

It is therefore an objective of the invention to provide a protective cover for a surgical instrument, in particular for a stapler, which enables precise, safe insertion and positioning of the surgical instrument in the patient's body at the point of use. In particular, the protective cover is intended to help determine the orientation of a mandrel to be extended from a head region of the stapler to optimally position or center the head region relative to a counterpart of the surgical instrument.

According to the invention, this problem is solved by a protective cover according to claim 1. Preferred embodiments of the invention are given in the dependent claims.

The invention relates to a protective cover for a surgical instrument, in particular for a stapler, comprising an outer sheath delimiting an inner space for at least partially covering a head region of the surgical instrument, and a pulling device which is connected to the outer sheath in a force-transmitting manner and comprises a pulling element. In the present case, the term "force-transmitting" refers to a connection between the outer sheath and the pulling device, which enables the force exerted on the pulling device to be transmitted to the outer sheath.

The term "direction of advancement" refers to the direction in which the protective cover and the surgical instrument are advanced or inserted into the body of a patient, e.g. into a bowel. The direction of advance essentially runs along a longitudinal axis of the protective cover.

A distal end of the protective cover thus denotes the foremost end of the protective cover when viewed in the direction of advancement. A proximal end of the protective cover designates the rearmost end of the protective cover when viewed in the direction of advancement. Consequently, the term "distal" refers to the side facing away from the user of the according to device the invention; correspondingly, the term "proximal" refers to the side facing closer to the user, for example the surgeon. For the sake of completeness, it should also be mentioned that other definitions of the terms "distal" and "proximal" are common in the medical field, but these are not used in the present application.

The surgical instrument, in particular the stapler or circular stapler, usually has a proximal actuating device, a shaft region connected to the actuating device and the head region connected to the shaft region.

The surgical instrument can have a centrally extending lumen for receiving and guiding an intraluminal instrument through the head region and possibly the shaft region. The intraluminal instrument can be designed as a mandrel device that can be extended from the head region. Conventional mandrel devices comprise an axially extending mandrel and an axially extending guide region connected to the mandrel. A mandrel device that protrudes axially from the head region and is firmly attached to the head region is also possible. Circularly arranged staples and a circular blade are built into the head region of the surgical instrument, in particular the stapler. The surgical instrument has a longitudinal axis and is at least approximately rotationally symmetrical to the longitudinal axis in order to enable the surgical instrument to be inserted into the patient's body.

In addition, the surgical instrument has a counterpart which is intended to be sewn into the hollow organ part which is arranged opposite the surgical instrument during an operation, before an actual connection of two hollow organ parts by means of stapling, in particular intestinal halves. The counterpart is further intended to receive the mandrel in a shaft of the counterpart.

In a preferred embodiment, the outer sheath has a half-shell-shaped, preferably essentially hemispherical cover region, which is centered on the longitudinal axis and is open proximally. The cover region can extend further proximally parallel to the longitudinal axis and comprise a jacket section, preferably in the form of a cylindrical jacket wall extending proximally. The provision of the jacket section gives the cover region the shape of a sleeve, which enables stable accommodation of the surgical instrument in the protective cover.

In a preferred embodiment, the outer sheath is rotationally symmetrical about the longitudinal axis in order to have an anatomically optimal shape, in particular with regard to insertion into the intestine, and to reduce friction during insertion.

The outer sheath has a dividing line which divides the outer sheath into at least a first segment and a second segment. Furthermore, the outer sheath comprises a connecting piece that connects the first segment and the second segment. The first segment and the second segment can be transferred from a covering position to a release position of the head region with the aid of a pulling device when a pulling force is exerted in a proximal direction on the pulling device. The connecting piece serves to prevent premature separation of the outer sheath in the covering position, for example when the protective cover placed on the surgical instrument is inserted into the bowel.

In a preferred embodiment, the dividing line is designed as a slit which divides the outer sheath into at least the first segment and the second segment and supports their separation during the transfer from the covering position to the release position.

Preferably, the dividing line is designed perforated, i.e. the dividing line runs from an inner side of the outer sheath to an outer side of the outer sheath. This embodiment makes it easy to separate the outer sheath. However, it is also conceivable to form the dividing line as a continuous predetermined breaking point, whereby at least one residual thickness of the outer sheath in the form of a film or a notch represents the predetermined breaking point.

In a preferred embodiment, the dividing line runs in a central plane containing the longitudinal axis in order to enable a symmetrical separation of the outer sheath into the first t and the second segment. This embodiment supports a symmetrical distribution of the pulling force exerted on the outer sheath, so that the protective cover is prevented from slipping onto the surgical instrument.

The connecting piece forms a predetermined breaking point, which is designed to break during the transfer from the covering position to the release position. The predetermined breaking point is designed in such a way that it breaks when a certain pulling force is applied.

In a preferred embodiment, the connecting piece can comprise webs. The webs connect the first segment and the second segment transversely to the dividing line, preferably in the circumferential direction of the outer sheath, and are preferably arranged opposite each other when viewed in the radial direction. This arrangement further supports a symmetrical distribution of the pulling force during the transfer to the release position. The design of the connecting piece is chosen in such a way that when the pulling device is pulled proximally, i.e. in the direction against the direction of advancement, a shock-like movement is minimized when the predetermined breaking point tears.

In a preferred embodiment, the connecting piece comprises two webs, i.e. a pair of webs, which each extend between the first segment and the second segment transversely to the dividing line in the circumferential direction of the outer sheath and are arranged opposite one another when viewed in the radial direction. This arrangement enables a particularly simple production as well as a minimum force for separating the outer sheath.

In a preferred embodiment, the connecting piece can comprise more than two webs, preferably two pairs of webs, particularly preferably three pairs of webs, which each extend in pairs between the first segment and the second segment transversely to the dividing line in the circumferential direction of the outer sheath and are arranged opposite each other when viewed in the radial direction. This arrangement enables a gradual separation of the predetermined breaking point and thus minimizes a shock-like movement when the predetermined breaking point tears. Furthermore, the number of webs can be selected depending on the desired force for separating the outer sheath.

It is also conceivable to form the webs as perforated sections which extend in pairs between the first segment and the second segment transverse to the dividing line, with the perforations penetrating the thickness of the web or extending only over part of the thickness. This solution also helps to further minimize shock-like movements during tearing.

In the covering position, the lips of the first segment and the second segment defined by the dividing line are at least approximately adjacent and the outer sheath thus delimits the interior space for at least partially accommodating the head region of the surgical instrument.

It is also possible to form the outer sheath in three, four or a variety of segments. This can be advantageous if smaller segments are required for the transfer from the covering position to the release position due to the shape of the surgical instrument, e.g. because of its asymmetry. The design of the dividing line and the connecting piece is adapted accordingly, in particular the number of webs and their arrangement to support the transfer to the release position.

In a preferred embodiment, corners formed at the intersection between the lips of the first segment and the second segment and a proximal edge of the outer sheath are rounded. The rounding of the lips serves to prevent injuries when the protective cover is pulled out. Particularly preferably, proximal end sections of the lips extend proximally with increasing distance from the central plane, measured in the circumferential direction, and in the form of a quarter circle concave to the central plane M. This design further minimizes the risk of injury.

According to the invention, the outer sheath comprises an orientation device arranged in its distal apex region and centered on the longitudinal axis, which is designed as a thickening of the apex region.

The thickening of the apex region gives the apex region a higher rigidity than the rest of the outer sheath, thus enabling an orientation function. The orientation device is thus designed to be stiffer than the rest of the outer sheath. As a result, it is possible to tactilely feel the location at which the mandrel will penetrate the previously closed organ wall, when fully extended. Furthermore, the thickened apex region exerts a mechanical resistance when the head region of the surgical instrument is moved during the search for the counterpart. In this case, the planned axial position of the mandrel can be adjusted to be optimally inserted into the counterpart. This avoids injury to organs during the search for the optimal position. Furthermore, the risk of the mandrel piercing the flanks of the orientation device is minimized.

The orientation device can thus be designed to feel the location of the piercing of the mandrel in the organ. The outer sheath is placed on the head region in such a way that the orientation device is located in the extension of the direction of the mandrel to be extended. The orientation device thus provides an indication of the location of the piercing of the mandrel when the mandrel is still protected in the head region. It follows that increased safety is achieved during the positioning of the head region.

Furthermore, the orientation device can be used to receive the mandrel, which is axially extended from the head region of the surgical instrument inserted into the protective cover. This can be advantageous for a special operation of the surgical instrument, in which the mandrel is at least partially extended before the protective cover is torn open and retracted. The orientation device keeps the outer sheath centered on the mandrel and stable on the head region of the surgical instrument. This arrangement enables the surgical instrument to be positioned securely at the point of use.

In a preferred embodiment, the outer sheath can have an opening, preferably circular, centered on the longitudinal axis, which opens into the orientation device. This opening enables a symmetrical distribution of the force when the outer sheath is torn open.

In a preferred embodiment, the orientation device protrudes on the side of the outer sheath facing away from the interior. This increases the mechanical resistance to the organ being palpated when the head region of the surgical instrument is moved during palpation.

In a preferred embodiment, the orientation device is designed as a thickening of the apex region extending distally along the longitudinal axis in a prismatic or cylindrical shape. These embodiments represent a simple design that can be manufactured inexpensively. In a prism-shaped embodiment, the orientation device forms a polygon-shaped surface, seen in cross-section, whose edge length can be between 0.5 mm and 12 mm. The number of corners and their shape, e.g. rounded or not rounded, evenly or unevenly distributed, symmetrically or asymmetrically distributed, can advantageously be selected to allow easy production, particularly during injection molding. In a cylindrical embodiment, the orientation device forms a circular surface when viewed in cross-section, the diameter of which can be between 3 mm and 12 mm. These embodiments are suitable for most staplers.

In a preferred embodiment, the orientation device is formed as a curved thickening of the apex region to reduce resistance when inserting the protective cover into the body. This embodiment contributes in particular to better control of the head region of the surgical instrument, e.g. for better control of a stapler head through the narrow anal canal of a patient.

Preferably, the orientation device is designed to taper distally, preferably in the shape of a truncated cone, to reduce the resistance when inserting the protective cover into the body. Viewed in longitudinal section, the orientation device can thus be of any conical shape.

The thickening can at least partially surround the opening and forms a guide channel extending along the longitudinal axis of the protective cover. The guide channel is intended to spatially shape the rigidity of the orientation device to optimize palpation. If necessary, the guide channel can also accommodate and guide the mandrel so that the protective cover remains centered on the mandrel in the direction of the longitudinal axis.

The guide channel is surrounded by an inner flank of the thickening. Furthermore, the thickening has an outer flank adjoining the inner flank and sloping downwards on the side facing away from the guide channel. In this context, the term "flank" defines a lateral, possibly inclined thickening wall.

The guide channel comprises a proximal guide channel opening at the end of the guide channel facing the interior and a distal guide channel opening at the end of the guide channel facing away from the interior.

Particularly preferably, the inner flank is formed directly adjacent to the edge of the opening. In other words, the inner flank starts directly at the edge of the opening so that the proximal guide channel opening corresponds to the opening. This prevents dirt particles and tissue from accumulating at the edge of the opening.

In a preferred embodiment, the guide channel has a constriction whose clear opening, viewed in a plane at right angles to the longitudinal axis, is dimensioned such that it can form a point of resistance when the mandrel is inserted. Specifically, the clear opening can be smaller than the largest cross-section of a tapered section of the mandrel. Consequently, it can be ensured that when the constriction is reached during the insertion of the mandrel into the guide channel, an increased resistance is generated, which can be interpreted as a signal or information about the axial position of the mandrel. This enables safe positioning of the surgical instrument, in particular the mandrel, at the point of use.

In a preferred embodiment, the thickening is in the form of a curved truncated cone. This shape supports easy insertion into the body.

In a preferred embodiment, a transition region of the thickening, which extends between the inner flank and the outer flank, is flattened or rounded. This design of the thickening also reduces the risk of injury from angular areas of the protective cover.

In a preferred embodiment, the cross-section of the guide channel is tapered, in particular continuously tapered, in order to make the orientation device axially rigid.

The cross-section of the guide channel, viewed in the direction of advancement, is particularly preferably tapered from the proximal guide channel opening, viewed in the direction of advancement. The funnel-shaped design of the guide channel enables a further form of design for the rigidity of the orientation device. In addition, the funnel-shaped design of the guide channel supports the insertion of the mandrel into the guide channel if the longitudinal axis of the protective cover, i.e. the guide channel, no longer quite coincides with the axial direction of the mandrel. This can occur, for example, when inserting the surgical instrument into the body if the protective cover placed on the surgical instrument in the covering position has moved sideways. During the insertion of the mandrel into the guide channel, the outer sheath returns to a position aligned with the longitudinal axis of the surgical instrument so that the protective cover optimally covers the head region in the covering position.

Preferably, the cross-section of the guide channel is conically tapered when viewed in the direction of advancement. This embodiment has the further advantage that it is easy to manufacture, particularly in an injection molding process.

In a preferred embodiment, the cross-section of the guide channel tapers in the shape of a cone to enable a symmetrical design of the guide channel and, if necessary, precise guidance.

In a preferred embodiment, the dividing line divides the orientation device into a first orientation element and a second orientation element, whereby the first orientation element is connected to the first segment and the second orientation element is connected to the second segment. When the protective cover is pulled out, this ensures that the orientation device, which separates into two parts, does not represent an obstacle that can get caught and can be removed together with the respective orientation elements.

In a preferred embodiment, the connecting piece also extends between the first orientation element and the second orientation element. This arrangement enables a regular distribution of the force for separating the outer cover. Furthermore, the guide channel is maintained as long as the protective cover is in the covering position.

In a preferred embodiment, the connecting piece can have a pair of webs between the first orientation element and the second orientation element and a pair of webs between the first segment and the second segment. This embodiment additionally enables simple manufacture of the outer sheath.

In a preferred embodiment, the connecting piece is only formed between the first orientation element and the second orientation element. This means that only the first orientation element and the second orientation element are connected by the connecting piece. This arrangement ensures that the guide channel is maintained as long as the protective cover is in the covering position.

In a preferred embodiment, the connecting piece can have only one pair of webs between the first orientation element and the second orientation element. This embodiment additionally enables a particularly simple production of the outer sheath as well as an optimum force for separating the outer sheath. In a preferred embodiment, the pulling device comprises a further pulling element. Preferably, the pulling element and the further pulling element run in a longitudinal plane which contains the longitudinal axis of the protective cover. This enables a symmetrical distribution of the pulling force on the outer cover. This prevents the protective cover from slipping off the head region of the surgical instrument when it is pulled.

Preferably, the pulling element and the further pulling element extend at a distance from each other that at least approximately corresponds to an outer diameter of the shaft region of the surgical instrument. The protective cover thus forms a compact unit together with the surgical instrument. Since the pulling elements run along the surgical instrument, the pulling force can also be exerted in the direction of the longitudinal axis of the surgical instrument when the protective cover is pulled out.

In a preferred embodiment, the pulling element is connected to the first segment via a projection section and the further pulling element is connected to the second segment via a further projection section. Preferably, the projection section and the further projection section extend in the longitudinal plane to also support optimum alignment of the pulling force.

The projection section and the further projection section can extend in their proximal end region at a distance from one another which at least approximately corresponds to the outer diameter of the surgical instrument, and in their distal end region at a distance from one another which at least approximately corresponds to the clear diameter of the outer sheath. The projection section and the further projection section thus form a transition region for optimum connection of the pulling elements to the outer sheath and transmission of the pulling force. This is achieved by adjusting the distance between the pulling elements to the distance that corresponds to the clear diameter of the outer sheath.

In a preferred embodiment, the pulling element and the further pulling element are connected via two spaced-apart, open rings, each of which is formed in a plane extending at least approximately at right angles to the longitudinal axis of the protective cover. The rings are designed to keep the distance between the pulling element and the further pulling element at least approximately constant. The diameter of the rings dimensioned in such a way that it at least approximately corresponds to the outer diameter of the surgical instrument. The pulling element and the further pulling element thus form a receiving region for the surgical instrument between the rings, which supports the axial positioning of the surgical instrument in the protective cover. The rings have the additional advantage that they prevent rotation of the pulling element and the further pulling element, particularly in the receiving region, during operation of the pulling device or during insertion into the body.

Preferably, the open rings each have an opening that can be formed on the same side of the longitudinal plane defined by the pulling element and the further pulling element. This makes it easy to insert the surgical instrument into the receiving region.

In a preferred embodiment, the pulling element and the further pulling element extend distally from the receiving region into the longitudinal plane and proximally to the receiving region at an increasing distance from the longitudinal plane when viewed proximally. In other words, in curved versions of the surgical instrument, in particular the stapler, the pulling element and the further pulling element follow a chord of the surgical instrument. Thus, the pulling elements follow the general longitudinal profile of the surgical instrument, and it is prevented that the pulling elements are too far away from the actuating device of the surgical instrument.

In a preferred embodiment, the pulling element and the further pulling element are connected at their proximal ends via a preferably semi-circular binding section. The binding section also helps to prevent the pulling device from getting caught in the surgical instrument. Furthermore, the binding section forms an optimal area for exerting the pulling force at least approximately axially, thus preventing the protective cover from tilting away from the head region.

In a preferred embodiment, the central plane and the longitudinal plane run at right angles to each other. In this way, the pulling force exerted on the pulling device can be distributed symmetrically to the central plane at the predetermined breaking points, while the outer sheath remains as centered as possible on the longitudinal axis.

In a preferred embodiment, the outer cover is rotationally symmetrical around the longitudinal axis. This enables an anatomically optimal insertion of the protective cover into the body and simple manufacture of the protective cover.

In a preferred embodiment, the protective cover is formed in one piece. The term "one-piece" should be understood to mean that the protective cover forms a single part, which can be produced by injection molding, for example, and that there is no seam. This is particularly advantageous to avoid interfaces in which dirt particles and fabric cannot accumulate. In this way, a safe and cost-effective device can be produced at the same time.

In addition, the protective cover can be integral, i.e. made from the same material. This further supports the simple and cost-effective manufacture of the protective cover.

The protective cover can be molded from an elastically and/or plastically deformable material such as a thermoplastic elastomer (TPE), a rubber or a thermoplastic that is suitable for medical applications. Such materials are known to the skilled person.

In a preferred embodiment, the surface of the outer sheath has tongue-shaped bulges extending from the distal to the proximal end of the outer sheath, preferably evenly distributed in the circumferential direction of the outer sheath and preferably of the same shape. The bulges cause the outer sheath to be aligned essentially parallel to the direction of insertion to facilitate insertion the protective cover into the body. Furthermore, the bulges reduce the risk of the head region getting caught in tissue folds when the surgical instrument is inserted. As a result, the outer sheath sits more stably on the head region of the surgical instrument when it is inserted. The curved structure of the outer sheath reduces tissue resistance when inserting the head region of the surgical instrument, in particular a stapler head, and thus contributes to better control of the head region of the surgical instrument, e.g. better control of the stapler head through the narrow anal canal of a patient.

In a preferred embodiment, the outer sheath comprises a circumferential support contour arranged in the interior for the axial positioning of the head region. The support contour is intended to determine the axial distance between the head region and the opening via the axial positioning of the head region in the outer sheath. This means that the position of the distal end of the mandrel, e.g. in the extended state, can be precisely predetermined and known in relation to the opening and possibly the distal guide channel opening. When the support contour is reached, it is also ensured that the head region is sufficiently inserted into the outer sheath so that the outer sheath does not tilt.

The support contour is in contact with the head region via a support contour surface, which is dimensioned in such a way that when the protective cover is pulled proximally, the outer sheath and thus the protective cover is at least approximately without shock-like movement when sliding over the head region.

In a preferred embodiment, the support contour is in the form of radially inwardly projecting projections that are evenly distributed and preferably uniformly formed in the circumferential direction of the outer sheath, the proximal end surfaces of which lie in a support contour plane extending at right angles to the longitudinal axis and form the support contour surface. As already mentioned, the support contour determines the axial position of the head region in the outer sheath. The support contour, formed as a variety of projections, allows to be pulled proximally at least approximately without a shock-like movement when sliding over the head region.

The clear diameter of the outer sheath proximal to the support contour plane corresponds at least approximately to the diameter of the head region to ensure centered and stable positioning of the surgical instrument, in particular the head region.

In a preferred embodiment, the support contour is designed as a bead running in the circumferential direction. The support contour is in contact with the head region via the support contour surface, which is dimensioned such that the clear diameter of the outer sheath proximal to the support contour plane corresponds to the diameter of the head region of a first surgical instrument and the clear diameter of the outer sheath distal to the support contour plane corresponds to the diameter of the head region of a second surgical instrument, wherein the diameter of the head region of the second surgical instrument is smaller than the diameter of the head region of the first surgical instrument. Thus, one size of the outer sheath fits on at least two sizes of the head of a surgical instrument.

The support contour, in particular the bead, can be formed by discrete protrusions distributed evenly or unevenly around the circumference or by closed contours. These designs also make it possible to accommodate two different diameters of the head regions.

Preferably, the surface of the interior distal to the support contour plane is smooth, i.e. free of protrusions or ribs, among other things, in order to enable simple manufacture and uniform distribution of forces.

In a preferred embodiment, the connecting piece is arranged distally to the support contour plane. This means that the connecting piece, i.e. the predetermined breaking point, only tears when the support contour slides onto the head region when the protective cover is pulled proximally.

As a first step in using the protective cover, the surgical instrument, in particular the stapler or circular stapler, is inserted into the protective cover until the head region has reached the support contour. In other words, the head region is inserted into the outer sheath and the shaft region into the receiving region so that the pulling device runs proximally along the longitudinal axis of the surgical instrument. The longitudinal axis of the surgical instrument and the protective cover are at least approximately aligned. The protective cover is centered on the head region in the covering position.

In a second step, the head region and, if necessary, part of the shaft section are inserted into the body, e.g. into the bowel. An operator inserts the head region, including the intraluminal instrument, into the bowel and pushes the surgical instrument forward in the direction of advancement to the point of use.

Due to the rounded shape of the protective cover, which also serves as a cover for the head region, no tissue folds, in particular mucous membrane folds, are pushed along, stretched and thus injured. In addition, the protective cover is held on the head region over the jacket wall, which also prevents injuries from the head region, e.g. from the edges of the head region.

When inserting and advancing the surgical instrument, the operator must ensure that the pulling device hangs out of the bowel at all times. This is optimally supported by the rings arranged between the pulling elements and the binding section at the end of the pulling elements.

The surgical instrument is advanced to a desired distance from the surgical site. The orientation device of the protective cover can be used to feel the location of the piercing of the intraluminal instrument, in this case the mandrel, in the bowel.

In a further step, the protective cover is torn open and pulled back. The operator pulls the pulling device proximally over the pulling elements. The pressure exerted must be sufficiently high to tear open the predetermined breaking points, i.e. the connecting piece. This separates the first segment and the first orientation element from the second segment and the second orientation element. In this way, the outer sheath is separated into two halves and transferred to the release position.

After positioning the surgical instrument, the operator preferably pulls back the protective cover until the head region is free. As the bowel is slightly stretchable in the radial direction, the two halves slide between the head region and the inner wall of the bowel by means of the pulling force and slide proximally. To prevent injury to the intestine or the intestinal mucosa during this direction of movement, all edges, e.g. the lips of the first segment and the second segment in their proximal end section, are rounded.

In the next step, the operator extends the intraluminal instrument from inside the head region. The mandrel perforates an adjacent bowel wall at the desired location. The shaft of the counterpart (a mushroom-shaped counterpressure plate) is then placed on the extended mandrel.

The mandrel is then retracted, and the tissue halves are clamped together so that a circular suture can be stapled to perform an anastomosis. Once the suture has been created and the partial tissue sections have been cut out in a ring shape with the circular knife, the surgical instrument is withdrawn together with the protective cover.

A method is thus disclosed for performing an anastomosis in which two tissue halves are sutured together using a surgical instrument at a surgical site, in particular using a stapler or a circular stapler, comprising the steps of:
a) providing the surgical instrument and a protective cover for the surgical instrument, in particular for the stapler, according to one of the embodiments disclosed above;
b) inserting a head region of the surgical instrument into an outer sheath of the protective cover and a shaft region of the surgical instrument into a receiving portion of the protective cover, wherein a pulling device of the protective cover extends proximally along the longitudinal axis of the surgical instrument and the protective cover is centered in a covering position on the head region;
c) insertion of the head region carrying the protective cover and possibly partly of the shaft region into the body of a patient, e.g. into a first vascular half of the intestine, including an intraluminal instrument of the surgical instrument, e.g. a mandrel device, and insertion up to a desired distance from the surgical site, wherein the surgical instrument may have a centrally extending lumen for receiving instrument through the head and guiding the intraluminal region and possibly the shaft region;
d) Palpating the location of the piercing of the intraluminal instrument in the bowel via the orientation device of the protective cover for positioning the head region and positioning the head region at the surgical site;
e) Tear open the protective cover and transfer the protective cover to a release position of the head region;
f) Pull back the protective cover proximally over the pulling device until the head region is free;
f) Moving the intraluminal instrument out of the interior of the head region;
g) Perforation through the intraluminal instrument of an adjacent intestinal wall of the first tissue half at the desired location and placement of a counterpart on the intraluminal instrument, which counterpart was sutured into the second tissue half of the intestine by means of stapling before an actual connection of a second tissue half with the first tissue half;
h) Retract the intraluminal instrument and clamp the two halves of the tissue together to form a circular suture using clamps and close the anastomosis.

The thickening of the apex region of the orientation device gives the apex region greater rigidity than the rest of the outer sheath, enabling an thus orientation function. Consequently, it is possible to use the orientation device to tactilely palpate the location at which the mandrel will penetrate the previously closed organ wall when fully extended. Furthermore, the thickened apex region exerts a mechanical resistance when the head region of the surgical instrument is moved during the search for the counterpart. In this case, the planned axial position of the mandrel can be adjusted to be optimally inserted into the counterpart. This avoids injury to organs during the search for the optimal position. Furthermore, the risk of the mandrel piercing the flanks of the orientation device is minimized.

For the sake of completeness, it should also be mentioned that deviations from the steps described above, e.g. a different sequence, are also conceivable depending on the circumstances.

Further advantages and features of the invention are shown in the following description of selected embodiments, which is explained with reference to the accompanying figures.

The protective cover 10 shown in FIG. 1 to FIG. 6 for a surgical: instrument 11, in particular for a stapler, comprises an outer sheath 12 for at least partially covering a head region 13 of the surgical instrument, and a pulling device 14 which is connected to the outer sheath 12 in a force-transmitting manner.

The outer sheath 12 has a half-shell-shaped, in the present case substantially hemispherical cover region 22, which is centered on a longitudinal axis L of the protective cover and is open proximally. The outer sheath 12 further comprises a jacket section which is connected to a proximal edge of the cover region 22 and which in the present case extends in the form of a cylindrical, proximally extending jacket wall 24. The outer sheath 12 is thus rotationally symmetrical about the longitudinal axis L.

In the present case, the outer envelope 12 is formed from a first segment 26 and a second segment 28, each of which lies on one side of a central plane M containing the longitudinal axis L and is separated by a dividing line 29 extending into the central plane M. In the present case, the dividing line is formed as a slit 29. Thus, the first segment 26 and the second segment 28 each represent one half of the outer envelope 12.

The first segment 26 and the second segment 28 are connected to each other by a connecting piece 30 in the form of two webs 31. The webs 31 connect the first segment 26 and the second segment 28 in the circumferential direction and, viewed in the radial direction, are arranged opposite one another in the cover region 22, as can also be seen in FIG. 5.

In a covering position, the outer sheath 12 thus delimits an interior space for at least partially accommodating the head region of the surgical instrument.

Proximal to the connecting piece 30, the slit 29 widens continuously in the circumferential direction and extends on both sides of the central plane M in the form of a quarter circle that is symmetrical and concave to the central plane M. This avoids angular edges in the proximal end region of the outer sheath 12.

In its distal apex region, the outer sheath 12 has an opening 38 centered on the longitudinal axis L.

Furthermore, the outer sheath 12 comprises an orientation device 40 arranged around the opening 38, which is designed as a thickening 40 of the apex region. The orientation device 40 is designed as a bead-shaped thickening 40 which tapers when viewed in the direction of advancement and which protrudes on the side of the outer sheath 12 facing away from the interior.

The thickening 40 surrounds the opening 38 and forms a guide channel 42 extending along the longitudinal axis L.

The guide channel 42 is surrounded by an inner flank of the thickening 40. Furthermore, the thickening 40 has an outer flank adjoining the inner flank and sloping downwards on the side facing away from the guide channel 42.

The guide channel comprises a proximal guide channel opening 42a on the end of the guide channel facing the interior and a distal guide channel opening 42b on the end of the guide channel 42 facing away from the interior, the inner flank being formed directly adjacent to the edge of the opening 38. The cross-section of the guide channel 42 is continuously tapered in the form of a cone when viewed in the direction of advancement. In the illustrated embodiment, the generatrix of the cone forms an angle $\alpha$ (alpha) of 16 degrees. The height of the thickening, measured from the opening 38, is approx. 5 mm.

The orientation device 40 is formed from a first orientation element 46 and a second orientation element 48, which are also each located on one side of the central plane M and are separated by the slit 29 extending into the central plane M. Thus, the first orientation element 46 and the second orientation element 48 each represent one half of the orientation device 40. The first orientation element 46 is integrally formed with the first segment 26 and the second orientation element 48 is integrally formed with the second segment 28.

The first orientation element 46 and the second orientation element 48 are also connected to one another by the connecting piece in the form of three pairs of further webs 50. The webs 50 connect the first orientation element 46 and the second orientation element 48 in the circumferential direction and, viewed in the radial direction, are arranged opposite one another in pairs, as can also be seen in FIG. 5.

The webs 31 and the further webs 50 form predetermined breaking points and are designed to break when moving from the covering position to a release position.

On the surface of the outer sheath 12, the outer sheath 12 has at least approximately elliptical bulges 52 extending radially outwardly from the distal apex region of the covering region 22 to the proximal end of the jacket wall 24, evenly distributed and uniformly formed in the circumferential direction of the outer sheath to facilitate insertion of the protective cover 10 into the intestine.

Figure 1:
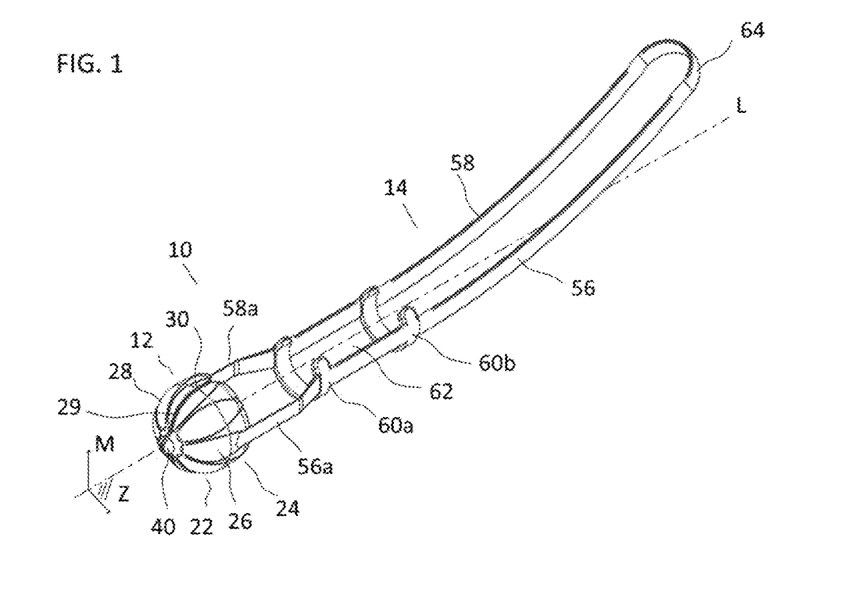
FIG. 1 a perspective view of a protective cover for a surgical instrument according to the invention.
Figure 2:
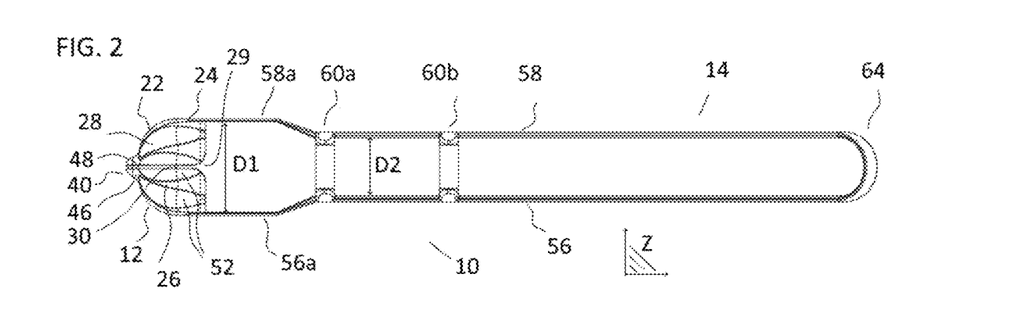
FIG. 2 a top view of the protective cover as shown in FIG. 1.
Figure 3:
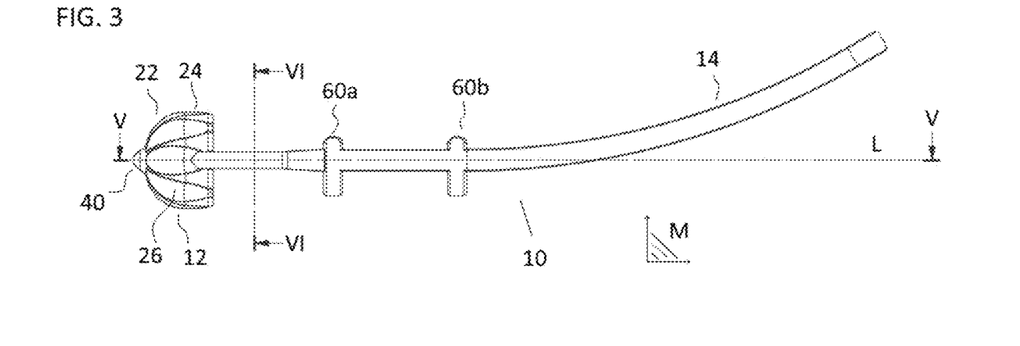
FIG. 3 a side view of the protective cover as shown in FIG. 1.
Figure 4:
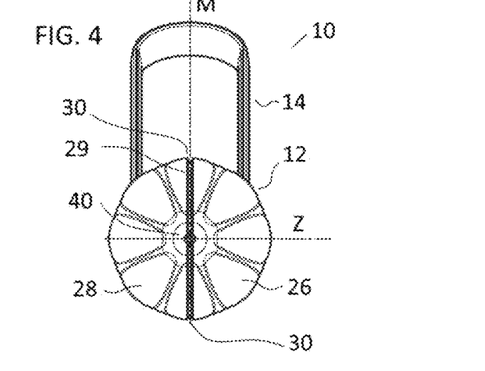
FIG. 4 a frontal view of the protective cover as shown in FIG. 1.
Figure 5:
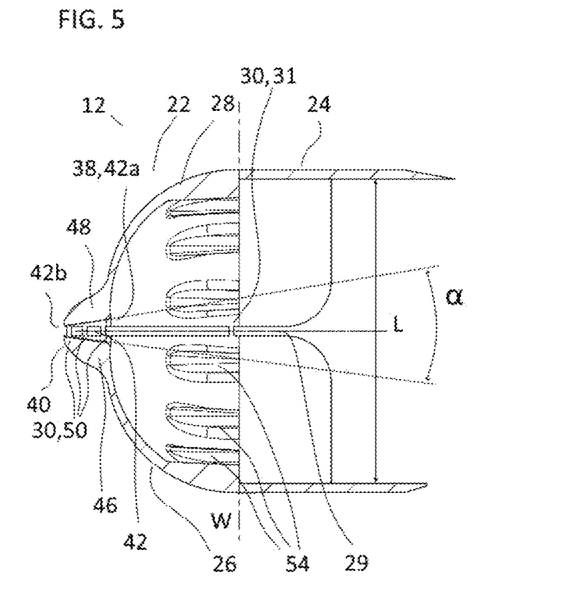
FIG. 5 a cross-section along line V-V through an outer sheath of the protective cover according to FIG. 1.
Figure 6:
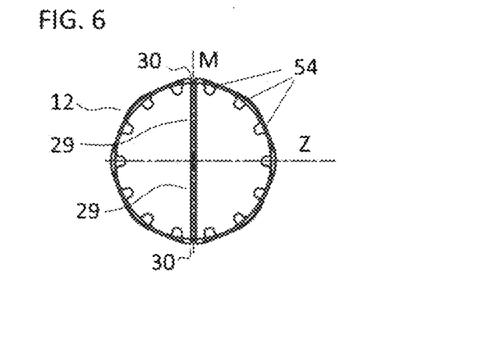
FIG. 6 a cross-section along line VI-VI through the outer sheath of the protective cover according to FIG. 1.

Furthermore, the outer sheath 12 comprises a circumferential support contour 54 arranged in the interior for axial positioning of the head region, as can be seen in FIG. 5 and FIG. 6. The support contour is in the form of radially 54 inwardly projecting projections which are evenly distributed and uniformly formed in the circumferential direction of the outer sheath 12 and whose proximal end surfaces lie in a support contour plane W extending at right angles to the longitudinal axis.

The clear diameter D1 of the outer sheath 12 proximal to the support contour plane W corresponds at least approximately to the diameter of the head region.

The pulling device 14 comprises a pulling element 56 and a further pulling element 58, which extend substantially in a longitudinal plane Z extending at right angles to the central plane M and encompassing the longitudinal axis L and at least approximately parallel to the longitudinal axis L. The pulling element 56 and the further pulling element 58 extend at a distance from one another which at least approximately corresponds to the outer diameter D2 of the surgical instrument.

The pulling element 56 is connected to the first segment 26 via a projection section 56a and the further pulling element 58 is connected to the second segment 28 via a further projection section 58a. The projection section 56a and the further projection section 58a also extend in the longitudinal plane Z.

In their distal end region, the projection section 56a and the further projection section 58a extend at least approximately parallel to the longitudinal axis L and at a distance from one another corresponding to the clear diameter D1.

In their proximal end region, i.e. facing away from the outer sheath, the projection section 56a and the further projection section 58a extend at a distance D2 from one another, which corresponds at least approximately to the outer diameter of a shaft region of the surgical instrument. The projection section 56a and the further projection section 58a thus form a transition region for adapting the distance between the pulling elements 56 and 58 to the distance corresponding to the clear diameter D1 of the outer sheath 12.

Figure 7:
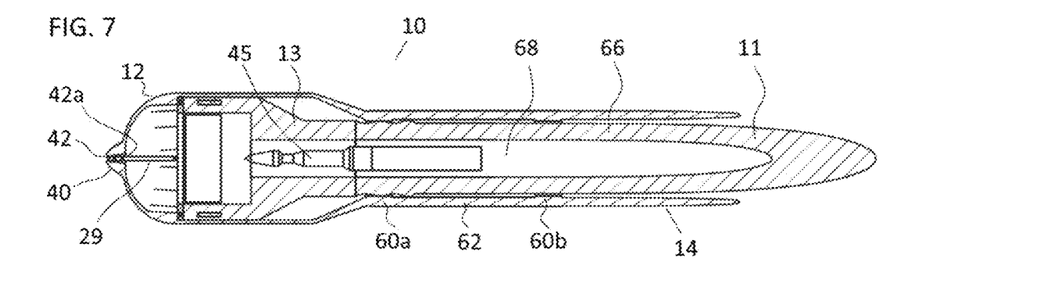
FIG. 7 a cross-section along line V-V through the protective cover according to FIG. 1, in which a surgical instrument is inserted.
Figure 8:
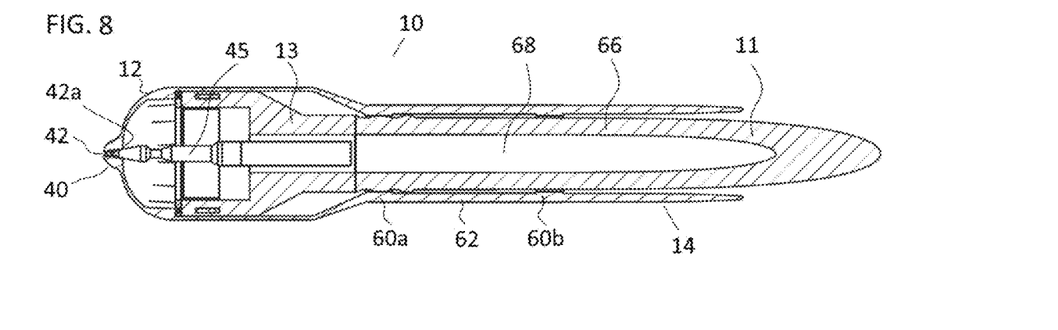
FIG. 8 the cross-section of FIG. 7, in which a mandrel of the surgical instrument is extended up to an orientation device of the protective cover.

The pulling element 56 and the further pulling element 58 are connected via two open rings 60a and 60b, which extend at right angles to the longitudinal axis L of the protective cover 10 and are spaced apart from one another, and which are each formed in a plane extending at right angles to the longitudinal axis of the protective cover. The rings are intended to keep the distance between the pulling element 56 and the further pulling element 58 at least approximately constant. The diameter of the rings 60a and 60b is dimensioned such that it corresponds to the outer diameter of the shaft region of the surgical instrument, as can be seen in FIG. 7 and FIG. 8. The pulling element 56 and the further pulling element 58 form a receiving region 62 for the surgical instrument between the rings 60a and 60b.

The rings 60a and 60b each have an opening which is formed on the same side of the longitudinal plane Z defined by the pulling element 56 and the further pulling element 58.

Distal to the receiving region 62, including into the receiving region 62, the pulling element 54 and the further pulling element 58 extend into the longitudinal plane Z. Proximal to the receiving region 62, the pulling element 54 and the further pulling element 58 extend proximally at an increasing distance from the longitudinal plane Z.

The pulling element 54 and the further pulling element 58 are connected together at their proximal ends via a semicircular binding section 64.

Figure 9:
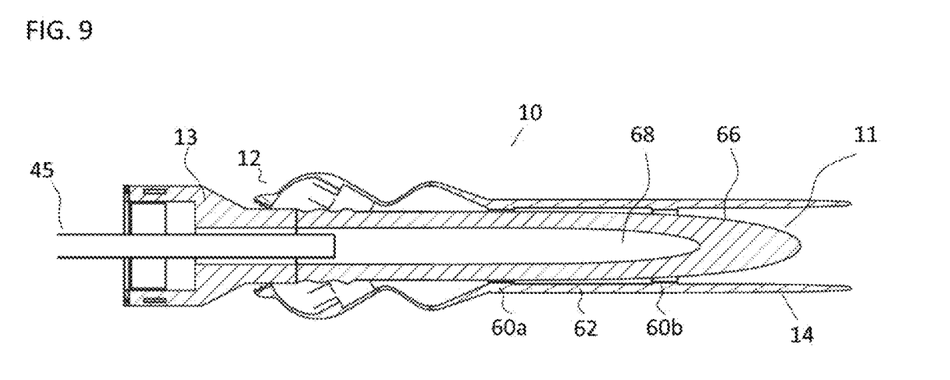
FIG. 9 the cross-section of FIG. 7, in which the protective cover has been partially pulled along the surgical instrument.
Figure 10:
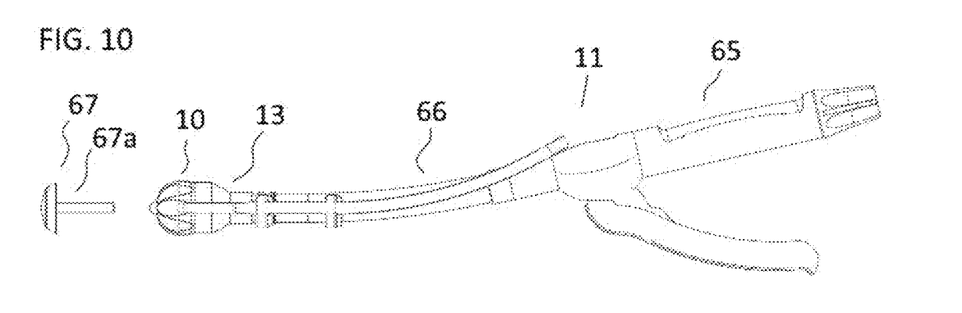
FIG. 10 a side view of the protective cover and the surgical instrument inserted in the protective cover.
Figure 11:
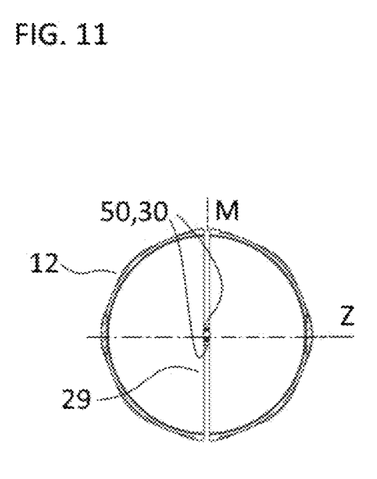
FIG. 11 a cross-section through the outer sheath of the protective cover of a further embodiment, similar to the cross-section in FIG. 6.
Figure 12:
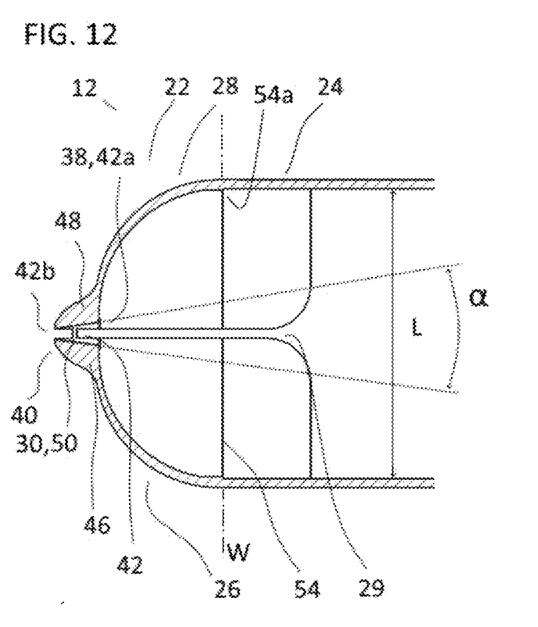
FIG. 12 a slightly enlarged view of a cross-section through the outer sheath of the protective cover as shown in FIG. 11, similar to the cross-section in FIG. 5.

The further embodiment of the protective cover 10 shown in FIG. 11 and FIG. 12 is similar to the embodiment in FIG. 1 to 10. The reference signs in FIG. 11 and FIG. 12 denote the same features as in FIGS. 1 to 10; only the differences are described below.

In FIG. 11 and FIG. 12, the support contour 54 is formed as a bead 54a extending in the circumferential direction. The support contour 54 is in contact with the head region 13 of the surgical instrument via the support contour surface, which is dimensioned such that the clear diameter of the outer sheath L proximal to the support contour plane W corresponds to the diameter of the head region.

In the present case, the surface of the interior distal to the support contour plane 54 is smooth. In contrast to the embodiment shown in FIG. 5, there are no ribs.

Further in contrast to the embodiment shown in FIG. 5, the connecting piece 30 extends only between the first orientation element 46 and the second orientation element 48. In the present case, the connecting piece 30 comprises a pair of webs, i.e. two webs 50, which each extend between the first segment 26 and the second segment 28 transversely to the slit 29 in the circumferential direction of the outer sheath 12 and, viewed in the radial direction, are arranged opposite one another.

It is therefore possible to also use the protective cover 10 with another head region that is smaller than the diameter of the head region. Thus, one size of the outer sheath fits at least two sizes of the head of a surgical instrument or of two different instruments.

With reference to FIG. 10, the surgical instrument 11, in particular the stapler or circular stapler, has a proximal actuating device 65, a shaft region 66 connected to the actuating device and the head region 13 connected to the shaft region 66. The shaft region 66 and the head region 13 have a centrally extending lumen 68 for receiving and guiding an intraluminal instrument, which in the present case is designed as a mandrel 45, as shown in FIGS. 7 to 9. The shaft region 66 and the head region 13 define a longitudinal axis of the surgical instrument and are at least approximately rotationally symmetrical to the longitudinal axis to simplify the insertion of the surgical instrument into the patient's body.

In addition, the surgical instrument 11 has a counterpart 67, which is intended to be sewn into the hollow organ part opposite the surgical instrument during an operation before an actual connection of two hollow organ parts, in particular intestinal halves, by means of stapling. The counterpart 67 is further intended to receive the mandrel 45 in a shaft 67a of the counterpart 67.

One possible use of the protective cover is described below for illustrative purposes. For the sake of completeness, it should be mentioned that deviations from the steps described below, e.g. a different sequence, are also conceivable depending on the circumstances. In a first step, the surgical instrument 11 is inserted into the protective cover 10. In other words, the head region 13 is inserted into the outer sheath 12 and the shaft region 66 is inserted into the receiving portion 62 so that the pulling device 14 extends proximally along longitudinal axis of the surgical instrument. The head region 13 is in contact with the support contour 54, as shown in FIG. 7. Since the protective cover 10 and the surgical: instrument 11 extend proximally to the receiving region 62 at an increasing distance from the longitudinal plane Z, only the head region and the distal part of the shaft region as well as the protective cover are visible in FIGS. 7 to 8 until shortly after the receiving region. The longitudinal axis of the surgical instrument and the protective cover are at least approximately aligned. The protective cover is centered on the head region 13 in the covering position.

In a second step, the head region 13 and, if necessary, part of the shaft region 66 are inserted into the body, e.g. into the intestine. An operator inserts the head region, including the mandrel, into the bowel and advances the surgical instrument in the direction of advancement towards the point of use.

Next, the operator can move the mandrel 45 out of the interior of the head region, as shown in FIG. 8. The distal end of the mandrel 45, i.e. the tip of the mandrel, first enters the opening 42a and then enters the guide channel 42 of the outer sheath 12. The mandrel is extended further distally until it reaches the constriction and experiences increased resistance during extension. The mandrel 45 remains protected by the outer sheath 12.

In a further step, the operator moves the mandrel 45 further out and pulls the pulling device 14 proximally over the pulling elements 56 and 58. The pressure exerted in the process is sufficiently great to tear open the predetermined breaking points, i.e. the connecting piece 30. Consequently, the first segment and the first orientation element are separated from the first segment and the second orientation element. The outer sheath 12 is thus separated into two halves, as shown in FIG. 9. By pulling the pulling device 14 in the direction opposite to the direction of advancement, the first segment 26 and the second segment 28 of the outer sheath 12 can be transferred from the covering position to the release position of the head region and the extended mandrel 45.

The two halves can be easily removed from the bowel by pulling the pulling device either in front of the stapler or together with it. As the bowel is slightly expandable in a radial direction, the two halves slip between the head region and the inner wall of the bowel by means of the pulling force and slide proximally.

LIST OF REFERENCE SIGNS

Protective cover 10
Surgical instrument 11
Outer sheath 12
Head region 13
Pulling device 14
Cover region 22
Jacket wall 24
First segment 26
Second segment 28
Dividing line, slit 29
Connecting piece 30
Webs 31
Opening 38
Orientation device 40
Guide channel 42
Proximal and distal guide channel opening 42a or 42b
Mandrel 45
First orientation element 46
Second orientation element 48
Further webs 50
Bulges 52
Support contour 54
Bead 54a
Pulling element 56
Projection section 56a
Further pulling element 58
Further projection section 58a
Rings 60a or 60b
Receiving region 62
Binding section 64
Actuating device 65
Shaft region 66
Counterpart 67
Lumen 68
Longitudinal axis L
Central plane M
Longitudinal plane Z
Support contour plane W

The invention claimed is:

1. A protective cover for a stapler as a surgical instrument comprising
an outer sheath delimiting an inner space for at least partially covering a head region of the surgical instrument inserted into the protective cover along a longitudinal axis thereof, and
a pulling device which is connected to the outer sheath in a force-transmitting manner and comprises a pulling element,
the outer sheath having a dividing line which divides the outer sheath into at least a first segment and a second segment,
the first segment and the second segment being separated by a connecting piece, which divides the outer sheath into at least the first segment and the second segment, wherein:
the first segment and the second segment are connected to one another by the connecting piece and can be transferred from a covering position into a release position of the head region with the aid of the pulling device,
the outer sheath comprises an orientation device which is arranged in its distal apex region, is centered on the longitudinal axis and is designed as a thickening of the apex region, and
the connecting piece has webs forming a predetermined breaking point which is intended to break during the transfer from the covering position to the release position.

2. The protective cover according to claim 1, wherein the orientation device is intended to sense the location of the piercing of a mandrel into an organ, which mandrel projects axially from the head region of the surgical instrument inserted into the protective cover.

3. The protective cover according to claim 1, wherein the orientation device protrudes on the side of the outer sheath facing away from the interior.

4. The protective cover according to claim 1, wherein the orientation device is designed as a distally tapering thickening of the apex region.

5. The protective cover according to claim 1, wherein the orientation device is of curved design.

6. The protective cover according to claim 1, wherein the orientation device is designed as a thickening of the apex region extending distally along the longitudinal axis in a prismatic or cylindrical shape.

7. The protective cover according to claim 1, wherein the dividing line divides the orientation device into a first orientation element and a second orientation element, the first orientation element being connected to the first segment and the second orientation element being connected to the second segment.

8. The protective cover according to claim 1, wherein the pulling device comprises a further pulling element, wherein the pulling element and the further pulling element extend in a longitudinal plane, which contains the longitudinal axis of the protective cover.

9. The protective cover according to claim 1, wherein the dividing line runs in a central plane, which contains the longitudinal axis of the protective cover.

10. The protective cover according to claim 1, wherein the outer sheath is designed to be rotationally symmetrical about the longitudinal axis.

11. The protective cover according to claim 1, wherein the surface of the outer sheath has tongue-shaped bulges extending from the distal to the proximal end of the outer sheath, evenly distributed and uniformly formed in the circumferential direction of the outer sheath.

12. The protective cover according to claim 1, characterized by a one-piece design.

13. The protective cover according to claim 1, wherein the outer sheath comprises a circumferential support contour arranged in its interior for axial positioning of the head region in the outer sheath.

14. The protective cover according to claim 13, wherein the support contour comprises projections which project radially inwards and are distributed in the circumferential direction of the outer sheath and whose proximal end faces lie in a support contour plane extending at right angles to the longitudinal axis.

* * * * *